(12) United States Patent
Wang et al.

(10) Patent No.: US 7,449,425 B2
(45) Date of Patent: Nov. 11, 2008

(54) PRODUCTION OF ALCOHOLS FROM SYNTHESIS GAS

(75) Inventors: Kun Wang, Bridgewater, NJ (US); Raymond A. Cook, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/230,088

(22) Filed: Sep. 19, 2005

(65) Prior Publication Data

US 2007/0004588 A1 Jan. 4, 2007

Related U.S. Application Data

(60) Provisional application No. 60/695,753, filed on Jun. 29, 2005.

(51) Int. Cl.
| B01J 23/00 | (2006.01) |
| B01J 21/00 | (2006.01) |
| B01J 29/00 | (2006.01) |
| B01J 20/00 | (2006.01) |

(52) U.S. Cl. .......................... 502/327; 502/73; 502/74; 502/80; 502/84; 502/324; 502/326; 502/328; 502/331; 502/332; 502/345; 502/346; 502/349; 502/350; 502/351; 502/355; 502/415; 502/439

(58) Field of Classification Search ................... 502/80, 502/84, 73, 74, 300, 324, 326, 327, 328, 502/331, 332, 345, 346, 349, 350, 351, 355, 502/415, 439

See application file for complete search history.

(56) References Cited

U.S. PATENT DOCUMENTS

| 4,288,558 | A |   | 9/1981 | Schmidt et al. | 518/716 |
| 4,377,643 | A |   | 3/1983 | Pesa et al. | 518/713 |
| 4,442,228 | A |   | 4/1984 | Leupold et al. | 518/714 |
| 4,902,660 | A | * | 2/1990 | Delzer et al. | 502/174 |
| 4,923,837 | A | * | 5/1990 | Fukuhara et al. | 502/84 |
| 4,929,762 | A | * | 5/1990 | Matsunaga et al. | 568/361 |
| 4,967,018 | A | * | 10/1990 | Soo et al. | 568/867 |
| 5,079,203 | A | * | 1/1992 | Pinnavaia et al. | 502/84 |
| 5,245,096 | A | * | 9/1993 | Derouane et al. | 585/419 |
| 5,318,936 | A | * | 6/1994 | Ferm et al. | 502/163 |
| 5,354,932 | A | * | 10/1994 | Bhattacharyya et al. | 585/400 |
| 5,399,537 | A | * | 3/1995 | Bhattacharyya et al. | 502/84 |
| 5,401,390 | A | * | 3/1995 | Ferm et al. | 208/207 |
| 5,407,652 | A | * | 4/1995 | Swamy et al. | 423/239.1 |
| 5,439,861 | A | * | 8/1995 | Bhattacharyya et al. | 502/84 |
| 5,441,630 | A | * | 8/1995 | Dai et al. | 208/216 PP |
| 5,472,677 | A |   | 12/1995 | Farris et al. | 423/239.1 |
| 5,653,774 | A |   | 8/1997 | Bhattacharyya et al. | 48/198.7 |
| 5,723,698 | A | * | 3/1998 | Dai et al. | 568/913 |
| 5,767,040 | A | * | 6/1998 | Bhattacharyya et al. | 423/594.3 |
| 5,914,293 | A | * | 6/1999 | Bhattacharyya et al. | 502/415 |
| 5,939,353 | A | * | 8/1999 | Bhattacharyya et al. | 423/600 |
| 6,376,405 | B1 | * | 4/2002 | Stamires et al. | 502/73 |
| 6,419,890 | B1 | * | 7/2002 | Li | 423/239.1 |
| 6,440,888 | B1 | * | 8/2002 | Stamires et al. | 502/80 |
| 6,444,188 | B1 | * | 9/2002 | Stamires et al. | 423/594.2 |
| 6,468,488 | B1 | * | 10/2002 | Stamires et al. | 423/239.1 |
| 6,514,473 | B2 | * | 2/2003 | Noweck et al. | 423/263 |
| 6,517,795 | B1 | * | 2/2003 | Noweck et al. | 423/263 |
| 6,652,828 | B2 | * | 11/2003 | Stamires et al. | 423/420.2 |
| 6,693,057 | B1 | * | 2/2004 | Cai et al. | 502/84 |
| 6,815,389 | B2 | * | 11/2004 | Stamires et al. | 502/80 |
| 6,953,488 | B2 | * | 10/2005 | Bhattacharyya et al. | 48/198.7 |
| 6,967,182 | B1 | * | 11/2005 | Olsbye et al. | 502/84 |
| 7,033,487 | B2 | * | 4/2006 | O'Connor et al. | 208/120.01 |
| 2003/0018219 | A1 | * | 1/2003 | Choudhary et al. | 568/319 |
| 2003/0172590 | A1 |   | 9/2003 | Bhattacharyya et al. | 48/198.7 |
| 2003/0203806 | A1 | * | 10/2003 | Vierheilig | 502/60 |
| 2004/0029729 | A1 | * | 2/2004 | Rytter et al. | 502/341 |
| 2005/0032632 | A1 |   | 2/2005 | Janssen | 502/84 |
| 2006/0275194 | A1 | * | 12/2006 | Gary | 423/417 |

OTHER PUBLICATIONS

Sels, B.F., et al, "Hydrotalcite-like Anionic Clays in Catalytic Organic Reactions," Catalysis Review, vol. 43(4), pp. 443-488 (2001).

Cavani, F., et al., "Hydrotalcite-type Anionic Clays: Preparation, Properties, And Applications," Catalysis Today, 1991, vol. 11(2), pp. 173-301.

Forzatti, P., et al, "Higher Alcohol Synthesis," Catal. Rev. Sci. Eng., 1991, vol. 33, pp. 109-168.

Smith, K.J., et al, "Development of a Kinetic Model for Alcohol Synthesis over a Cesium-Promoted Cu/ZnO," Ind. Eng. Chem. Res., 1991, vol. 30, pp. 61-71.

Stiles, A.B., et al, "Catalytic Conversion of Synthesis Gas to Methanol and Other Oxygenated Products," Ind. Eng. Chem. Res. 1991, Vo. 30, pp. 811-821.

Cornilis, B., et al, "Applied Homogeneous Catalysis with Organometallic Compounds," vol. 2, pp. 902-914, Wiley-VCH, New York, 1996.

Masaru I chikawa, "Bimetallic C luster-Derived H eterogeneous Catalysts-Heteronuclear T wo-Site Activation of CO in Syngas Conversion to Oxygenates," Polyhedron vol. 7, No. 22/23, pp. 2351-2367, 1988.

* cited by examiner

*Primary Examiner*—Cam N. Nguyen

(57) ABSTRACT

The invention relates to a catalyst composition, a method of making the same and its use in a process for converting synthesis gas to alcohols. The catalyst composition comprises an anionic clay hydrotalcite and a catalytically active metal component, such as rhodium, manganese, cobalt, copper, and a mixture thereof.

5 Claims, No Drawings

PRODUCTION OF ALCOHOLS FROM SYNTHESIS GAS

CROSS REFERENCE TO RELATED APPLICATIONS

This application claims the benefit of Provisional Application No. 60/695,753 filed Jun. 29, 2005, the disclosure of which is fully incorporated herein by reference.

FIELD OF INVENTION

The present invention relates to a catalyst for the production of alcohols from synthesis gas, to a method of producing the catalyst and to the use of the catalyst in alcohol production.

BACKGROUND OF INVENTION

Lower alcohols, such as methanol and ethanol, are important commodity chemicals. For example, lower alcohols, and especially methanol, can be converted to olefins and offer an important route to olefin production that employs non-petroleum sources. In a typical methanol-to-olefin (MTO) reaction, ethylene and propylene are produced in roughly equal yields. However, there are significant economic incentives to produce more ethylene. It has been demonstrated that ethylene selectivity can be significantly improved by co-feeding a small amount of ethanol (5-10 wt. %) with the methanol.

Methanol is commercially produced from synthesis gas (syngas) using copper-based catalysts under forcing conditions (200-300° C. and 50-100 atm). However, due to equilibrium limitations, one-pass conversion is relatively low and so recycle of a large amount of gas is required. Moreover, this process is highly selective to methanol (95+%), with only a small amount of ethanol being formed when high temperatures and low feed rates are employed.

Methanol, the preferred alcohol for light olefin production, is typically synthesized from the catalytic reactions of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred process for converting a feedstock containing methanol into one or more olefin(s), primarily ethylene and/or propylene, involves contacting the feedstock with a molecular sieve catalyst composition.

Ethanol is produced commercially either by fermentation or by ethylene hydration catalyzed by an acid catalyst. Alternative routes have been proposed in the literature, including 1) methanol homologation (reaction of methanol with syngas giving ethanol, catalyzed by rhodium, manganese, ruthenium, iron, or cobalt as described in *Applied Homogeneous Catalysis with Organometallic Compounds*, vol. 2, edited by B. Cornils and W. A. Herrmann, pages 902 to 914, VCH, New York, 1996); and 2) direct synthesis from syngas using supported noble metals such as rhodium as described by Ichikawa (Polyhedron, vol. 7, No. 22/23, pp. 2351-2367, 1988). The homologation route is characterized by harsh reaction conditions (e.g., >300 atm for the Co catalysts), low activity, and low selectivity (the products contain various amounts of acetaldehyde, esters, and even acetic acid). The activities for supported rhodium systems are also low and the products also contain impurities such as acetaldehyde and hydrocarbons.

Direct synthesis of mixed alcohols from syngas has been extensively explored and even tested at pilot scales. Traditionally, the catalysts for mixed alcohol synthesis can be categorized into three groups as discussed in many publications (e.g., P. Forzatti, et al., Catal. Rev.—Sci. Eng., vol. 33 No. 1-2, pp. 109-168, 1991.): 1) mixed metal oxides made via co-precipitation and promoted with alkali metals such as sodium, potassium, rubidium, or cesium; 2) cobalt supported on molybdenum sulfide ($Co/MoS_2$) promoted with potassium; and 3) noble metals supported on an oxide support as discussed in the previous paragraph. However, the driver for mixed alcohol synthesis in the art was to make fuel-grade alcohol mixtures so that they could be blended with gasoline as motor vehicle fuels. Indeed, a wide range of alcohols ($C_1$—$C_6OH$, both linear and branched), significant amounts of paraffins, and even small amounts of olefins are formed from both the mixed metal oxides system and the molybdenum sulfide supported cobalt ($Co/MoS_2$) system and, in many cases, iso-butanol is the major component among the higher alcohols. Iso-butanol is an undesired feed for MTO because it produces predominantly iso-butene, together with oxygenates and coke.

There is a current need for a low-cost route for converting syngas to a methanol/ethanol mixture which contains little or no higher alcohols and which can therefore be fed directly into an MTO process. According to the invention, it has been found that a catalyst comprising a catalytically active metal component on an anionic clay support, such as a hydrotalcite, is effective to convert syngas to a product containing methanol, ethanol, and only small amounts of higher alcohols and other oxygenates.

U.S. Pat. No. 5,472,677 discloses a process for removing $N_2O$ from an $N_2O$-containing gaseous mixture by contacting the gaseous mixture with a catalyst produced by heat treating an anionic clay material, such as a hydrotalcite. Example 5 of this patent describes the synthesis of a cobalt-rhodium, aluminum hydrotalcite in which a solution of 1.0 g (10% Rh) rhodium nitrate, 28.81 g cobalt nitrate hexahydrate and 18.76 g of aluminum nitrate nonahydrate in 114 cc of distilled water is added dropwise (over a half-hour period at room temperature) to a 114 cc solution of 14.44 g 97% NaOH and 10.02 g sodium carbonate while maintaining the temperature at or below room temperature. The precipitate is stirred for 2 hours, heated to 65° C. for 18 hours, filtered, washed with large amounts of distilled water to remove excess sodium and nitrate, and dried at 110° C. to produce the desired clay.

U.S. Patent Application Publication No. 2005/0032632, published Feb. 10, 2005, discloses a catalyst composition for use in the conversion of a oxygenated feedstock, such as methanol, into one or more olefin(s), preferably ethylene and/or propylene, wherein the catalyst composition comprises a molecular sieve, such as a silicoaluminophosphate and/or an aluminophosphate, hydrotalcite, and optionally a rare earth metal component, such as lanthanum, yttrium, cerium and mixtures thereof.

U.S. Patent Application Publication No. 2003/0172590, published Sep. 18, 2003, discloses a process for the preparation of synthesis gas from a feedstock containing methane and/or higher hydrocarbons having from about 2 to about 12 carbon atoms by an initial catalytic treatment of the feedstock to provide a methane-containing gaseous mixture substantially free of compounds having 2 or more carbon atoms, and then reforming the gaseous mixture at elevated temperatures using a catalyst obtained by heat treating a nickel-containing hydrotalcite clay.

U.S. Pat. No. 5,653,774 discloses a method for preparing synthesis gas comprising feeding water and a gaseous or vaporizable hydrocarbyl compound to a reaction zone containing a catalyst comprising the composition formed by heat treating under reforming conditions including a temperature of at least 700° C., a catalyst precursor composition comprising at least one hydrotalcite compound having formula:

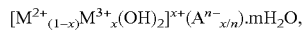

wherein $M^{2+}$ is a metal ion having a valence of 2+ and is at least $Ni^{2+}$ ions; $M^{3+}$ is a metal ion having a valence of 3+; x is a number of about 0.10 to about 0.50; $A^{n-}$ is an anion having a negative charge of n; and m is 0 or a positive number. The heat treating converts the hydrotalcite to a new spinel phase; and under reforming conditions the $M^{2+}$ component is at least partially reduced to produce metal particles of about 1 to about 1000 nanometers in size and containing at least nickel in the zero oxidation state.

U.S. Pat. No. 4,377,643 discloses a process for upgrading syngas to alkanes and alcohols by contacting the syngas with a catalyst comprising mixed oxides of ruthenium, copper, at least one alkali metal and at least one of rhodium, iridium, palladium, and platinum. The catalyst can also include carrier selected from alumina, silica, alumina-silica, alundum, clay, and silicon carbide.

U.S. Pat. No. 4,442,228 discloses a process for the manufacture of ethanol by catalytically reacting carbon monoxide and hydrogen at a temperature in the range of 175° C. to 375° C. and a pressure in the range of 1 to 300 bar in the presence of a supported rhodium catalyst consisting of a rhodium component and at least one co-catalyst selected from the group consisting of zirconium, hafnium, lanthanum, platinum, chromium and mercury wherein said rhodium component and co-catalyst are applied by impregnation onto a catalyst carrier of silicic acid or silicates of elements of Groups II to VIII of the Periodic Table.

SUMMARY OF INVENTION

In one aspect, the invention resides in a alcohol synthesis catalyst comprising:
(a) at least one catalytically active metal or metal compound, wherein said catalytically active metal is selected from Groups 3 to 15 of the Periodic Table of the Elements; and
(b) an anionic clay having the formula:

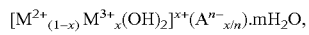

wherein $M^{2+}$ is a metal ion having a valence of 2+, $M^{3+}$ is a metal ion having a valence of 3+, x is a number of about 0.10 to about 0.50, $A^{n-}$ is an anion having a negative charge of n, and m is 0 or a positive number, and wherein $M^{2+}$ and $M^{3+}$ are different from said at least one catalytically active metal.

Conveniently, said anionic clay comprises a hydrotalcite clay.

Conveniently, said catalytically active metal is selected from Groups 6 to 12 of the Periodic Table of the Elements, preferably rhodium, manganese, cobalt, copper, chromium, molybdenum, nickel, palladium, platinum, ruthenium, iron, zinc and mixtures thereof.

Conveniently, said catalytically active metal is present in an amount between about 0.01 and about 20 weight % of the total catalyst on an elemental metal basis.

In another aspect, the invention resides in a process for producing a mixed alcohol synthesis catalyst comprising:
(a) providing an anionic hydrotalcite clay;
(b) treating said clay with a solution comprising at least one catalytically active metal compound, wherein said catalytically active metal is selected from Groups 3 to 15 of the Periodic Table of the Elements;
(c) drying the treated clay produced in (b); and
(d) calcining the dried, treated clay produced in (c).

Conveniently, said catalytically active metal is selected from Groups 6 to 12 of the Periodic Table of the Elements, preferably rhodium, manganese, cobalt, copper, chromium, molybdenum, nickel, palladium, platinum, ruthenium, iron, nickel, zinc and mixtures thereof.

Conveniently, said drying is conducted at a temperature of from about 50° C. to about 200° C. and said calcining is conducted at a temperature of from about 300° C. to about 550° C.

In yet another aspect, the invention resides in a process for producing alcohols comprising contacting a feed comprising carbon monoxide and hydrogen under alcohol synthesis conditions with a catalyst comprising an anionic hydrotalcite clay and a catalytically active metal component to produce an effluent comprising at least one alcohol.

Conveniently, said catalytically active metal component comprises at least one metal or compound thereof selected from Groups 3 to 15 of the Periodic Table of the Elements.

Conveniently, said at least one alcohol comprises methanol and more preferably comprises methanol and ethanol.

In one embodiment, said at least one alcohol is separated from said effluent. In another embodiment, said effluent is fed directly to an oxygenate to olefin conversion process.

DETAILED DESCRIPTION OF THE EMBODIMENTS

The invention is directed to a catalyst composition, its production and its use in the manufacture of alcohols from synthesis gas. In particular, the invention is based on the discovery that a catalyst composition comprising a catalytically active metal component on an anionic clay support, such as a hydrotalcite, can be effective to convert syngas to a product containing methanol and ethanol, and in some cases only small amounts of higher alcohols and other oxygenates. As a result the alcohol-containing product can provide an attractive feedstock to a process for converting methanol/ethanol to light olefins, particularly light olefins rich in ethylene.

Catalytically Active Metal Component(s)

The catalytically active metal component(s) employed in the alcohol synthesis process of the invention can be any metal(s), or compound(s) thereof, selected from Groups 3 to 15 of the Periodic Table of the Elements. Preferred metals are selected from Groups 6 to 12 of the Periodic Table of the Elements and include rhodium, manganese, cobalt, copper, chromium, molybdenum, palladium, platinum, ruthenium, iron, nickel, zinc and mixtures thereof, especially rhodium, manganese and mixtures thereof.

The amount of catalytically active metal or metal compound present in the catalyst of the invention is not closely controlled and will typically vary with the particular metal or metal compound employed. In general, however, the catalytically active metal or metal compound is present in an amount between about 0.01 and about 20 weight %, such as between about 1 and about 10 weight %, of the total catalyst on an elemental metal basis.

In general, the oxidation state of the metal in the final catalyst is not critical, but generally the metal will be present in a lower oxidation state or in the zero valent or elemental metal state after pretreatment before the onset of the alcohol synthesis reactions.

Anionic Clay Support

The support employed in the catalyst of the invention is derived from an anionic clay and in particular a hydrotalcite clay. Hydrotalcite is a naturally occurring mineral found in relatively small quantities in a limited number of geographical areas, principally, in Norway and in the Ural Mountains. Natural hydrotalcite has a variable composition depending on the location of the source. Natural hydrotalcite is a hydrated magnesium, aluminum and carbonate-containing composition, which has been found to have the typical composition, represented as $Mg_6Al_2(OH)_{16}CO_3 \cdot 4H_2O$. Natural hydrotalcite deposits are generally found intermeshed with spinel and other minerals, such as penninite and muscovite, from which it is difficult to separate the natural hydrotalcite.

Synthetically produced hydrotalcite can be made to have the same composition as natural hydrotalcite, or, because of flexibility in the synthesis, it can be made to have a different composition by replacing the carbonate anion with other anions, such as phosphate ion. In addition, the type and ratio of the divalent and trivalent metal ions can be varied to control the basic properties of the hydrotalcite. In general, the hydrotalcite-like compounds usesful in the catalyst of the invention comprise the formula:

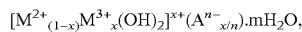

$$[M^{2+}_{(1-x)}M^{3+}_x(OH)_2]^{x+}(A^{n-}_{x/n}) \cdot mH_2O,$$

wherein $M^{2+}$ is a metal ion having a valence of 2+, $M^{3+}$ is a metal ion having a valence of 3+, x is a number of about 0.10 to about 0.50, $A^{n-}$ is an anion having a negative charge of n, and m is 0 or a positive number, and wherein $M^{2+}$ and $M^{3+}$ are different from said at least one catalytically active metal.

$M^{2+}$ is preferably selected from $Mg^{2+}$, $Ca^{2+}$, $Ni^{2+}$, $Cd^{2+}$, $Co^{2+}$, $Cu^{2+}$, $Fe^{2+}$, $Mn^{2+}$, $Pd^{2+}$, $Pt^{2+}$, $Sr^{2+}$, $Ti^{2+}$, $V^{2+}$, $Zn^{2+}$, $Zr^{2+}$, or a mixture thereof $M^{3+}$ is preferably selected from $Al^{3+}$, $B^{3+}$, $Cr^{3+}$, $Fe^{3+}$, $Mn^{3+}$, $Ni^{3+}$, $Co^{3+}$, $Ga^{3+}$, $In^{3+}$, $Rh^{3+}$, $Ti^{3+}$, $Tl^{3+}$, $V^{3+}$, the trivalent lanthanum metal ions, or a mixture of more than one of said trivalent metal ions. Preferably $M^{3+}$ is at least $Al^{3+}$.

The anion, $A^{n-}$, in the formula above can be any anion that provides for a hydrotalcite-like structure and can be, for example, carbonate, nitrate, halide (e.g. $Cl^-$, $Br^-$), chlorate, sulfate, hydroxide, oxide, carboxylates and polycarboxylates; particularly those having one to about 20 carbon atoms, including, for example, acetate, benzoate, the phthalates, and the like, phosphates, boron containing anions, metalates of metals from Group 5 of the Periodic Table of Elements, metalates of metals of Group 6 of the Periodic Table.

The value x is about 0.1 to about 0.5, preferably 0.25 to about 0.45. The value n is suitably about 1 to about 10. The amount of water present in the hydrotalcite-like catalyst precursor is variable. The amount of water can be such that the value m in the formula above is about 0 to about 2.

A phosphate-modified synthetic hydrotalcite and a process for its synthesis are disclosed in U.S. Pat. No. 4,883,533. U.S. Pat. No. 3,539,306 discloses a process for preparing hydrotalcite which involves mixing an aluminum-containing compound with a magnesium-containing compound in an aqueous medium in the presence of carbonate ion at a pH of at least 8. U.S. Pat. No. 4,656,156 discloses a process for producing synthetic hydrotalcite by heating a magnesium compound to a temperature of about 500 to 900° C. to form activated magnesia, adding the activated magnesia to an aqueous solution containing aluminate, carbonate and hydroxyl ions, and then agitating the resultant mixture at a temperature of about 80 to 100° C. for 20 to 120 minutes to form a low density, high porosity hydrotalcite. A similar process is disclosed in U.S. Pat. No. 4,904,457. The entire disclosure of each of the above references is incorporated herein by reference.

Hydrotalcite compositions containing pillaring organic, inorganic and mixed organic/inorganic anions are disclosed in U.S. Pat. No. 4,774,212, the entire disclosure of which is incorporated herein by reference. The compositions are anionic magnesium aluminum hydrotalcite clays having large inorganic and/or organic anions located interstitially between positively charged layers of metal hydroxides.

An aggregated synthetic hydrotalcite having a substantially spheroidal shape and an average spherical diameter of up to about 60 μm, composed of individual platy particles, is disclosed in U.S. Pat. No. 5,364,828, the entire disclosure of which is incorporated herein by reference. This form of hydrotalcite is prepared from aqueous solutions of soluble magnesium and aluminum salts, which are mixed in a molar ratio of from about 2.5:1 to 4:1, together with a basic solution containing at least a two-fold excess of carbonate and a sufficient amount of a base to maintain the pH of the reaction mixture in the range of from about 8.5 to about 9.5.

A nickel-containing hydrotalcite and a method for its synthesis are described in U.S. Pat. No. 5,653,774, the entire contents of which are incorporated herein by reference.

One particularly suitable hydrotalcite useful as the catalyst support of the invention is commercially available and, for example, can be obtained from Sasol North America Inc. as Condea Pural MG.

Method of Making the Catalyst Composition

The catalyst composition used herein can be prepared using a variety of methods. In general, however, making the catalyst composition comprises initially dissolving a compound of the or each desired catalytically active metal in a solvent, such as water or a mineral acid, or an organic solvent such as acetone, ethanol, methanol, tetrahydrofuran, acetonitrile, or ethylene glycol, combining the resultant solution(s) with the hydrotalcite clay either by impregnation or slurry mixing and then drying the resultant mixture. Suitable metal compounds include acetates, halides, oxides, oxyhalides, hydroxides, sulfides, sulfonates, borides, borates, carbonates, nitrates, carboxylates, tartrates, oxalates, oxynitrates, other soluble inorganic or organometallic precursors and mixtures thereof. Suitable drying conditions include a temperature of about 50° C. to about 200° C., such as about 75° to about 150° C., for a time of about 1 hour to about 24 hours, for example about 2 hours to about 12 hours.

The resultant catalyst composition can then be formed into useful shaped and sized particles by well-known techniques such as spray drying, pelletizing, extrusion, and the like.

Once the catalyst composition is formed in a substantially dry or dried state, to further harden and/or activate the formed catalyst composition, a heat treatment such as calcination, at an elevated temperature is usually performed. Typical calcination temperatures are in the range and said calcining is conducted at a temperature of from about 300° C. to about 550° C., such as from about 350° C. to about 450° C. Typical calcination environments are air (which may include a small amount of water vapor), nitrogen, helium, flue gas (combustion product lean in oxygen), or any combination thereof. Calcination times can vary between about 1 and about 20 hours, such as between about 3 to about 10 hours.

Alcohol Synthesis Process

The alcohol synthesis process of the invention comprises contacting synthesis gas, generally referred to as "syngas", which is a mixture of carbon monoxide, hydrogen and optionally carbon dioxide, with the catalyst composition described above under conditions to sustain the following reactions:

$$CO + 2H_2 \rightarrow CH_3OH$$

$$CO_2 + 3H_2 \rightarrow CH_3OH + H_2O$$

$$2CO + 4H_2 \rightarrow C_2H_5OH + H_2O$$

$$2CO_2 + 6H_2 \rightarrow C_2H_5OH + 3H_2O$$

The syngas feed to alcohol synthesis process of the invention can be produced in a variety ways well-known in the art, such as steam reforming and partial oxidation of hydrocarbons, especially methane. An alternative process involves autothermal reforming, which combines some of the features of steam reforming and partial oxidation in that a hydrocarbon feed, such as $CH_4$, is reacted with steam and air to from hydrogen, carbon monoxide and carbon dioxide. Typically, the syngas product is cooled prior to being sent to the alcohol synthesis reactor so as to condense at least a portion of the water vapor formed during the syngas process.

Desirably, the syngas input to the alcohol synthesis reactor has a molar ratio of hydrogen ($H_2$) to carbon oxides (CO+ $CO_2$) in the range of from about 0.5:1 to about 20:1, preferably in the range of from about 1:1 to about 10:1. In another embodiment, the syngas has a molar ratio of hydrogen ($H_2$) to carbon monoxide (CO) of at least 2:1. Carbon dioxide is optionally present in an amount of not greater than 50% by volume, based on total volume of the syngas.

The $CO_2$ content, relative to that of CO, in the syngas should be high enough so as to facilitate the reaction rates and to minimize the amount of undesirable by-products such as paraffins. At the same time, the relative $CO_2$ to CO content should not be too high so as to reduce alcohol yield. Desirably, the syngas contains $CO_2$ and CO at a molar ratio of from about 0.01 to about 1.2, preferably from about 0.05 to about 1.0.

The alcohol synthesis process of the invention is effective over a wide range of temperatures. In one embodiment, the syngas is contacted with the alcohol synthesis catalyst at a temperature in the range of from about 302° F. (150° C.) to about 842° F. (450° C.), preferably in a range of from about 347° F. (175° C.) to about 662° F. (350° C.), more preferably in a range of from about 392° F. (200° C.) to about 572° F. (300° C.).

The process is also operable over a wide range of pressures. In one embodiment, the syngas is contacted with the alcohol synthesis catalyst at a pressure in the range of from about 15 atmospheres to about 125 atmospheres (1515 to 12625 kPa), preferably in a range of from about 20 atmospheres to about 100 atmospheres (2020 to 10100 kPa), more preferably in a range of from about 25 atmospheres to about 90 atmospheres (2525 to 9090 kPa).

Gas hourly space velocities vary depending upon the type of continuous process that is used. Desirably, gas hourly space velocity of flow of gas through the catalyst bed is in the range of from about 50 hr-1 to about 50,000 hr-1. Preferably, gas hourly space velocity of flow of gas through the catalyst bed is in the range of from about 250 hr-1 to about 25,000 hr-1, more preferably from about 500 hr-1 to about 10,000 hr-1.

The alcohol synthesis process of the invention can be conducted as a batch process or a continuous processes. Continuous processes are preferred. Tubular bed, slurry bubble-column and fluidized bed processes are particularly preferred types of continuous processes.

The product of the alcohol synthesis process typically comprises about 10 wt % to 80 wt % of methanol and ethanol, in which the methanol to ethanol weight ratio varies between about 0.2:1 and about 15:1. In addition, the product normally contains about 2 wt % to 45 wt % of other oxygenates, such as dimethyl ether, with the remainder mainly being water and lower hydrocarbons, particularly methane. The product generally contains less than 10 wt % of higher alcohols, such as iso-butanol.

The crude product from the alcohol synthesis reaction can be further processed by conventional separation techniques, such as adsorption and/or distillation, to remove the water and hydrocarbon impurities and even divide the methanol and ethanol into separate product streams. Alternatively, the product can be fed directly to a process for converting oxygenates to olefins (OTO), either with or without initial removal of the water and/or hydrocarbon impurities.

Conversion of Methanol to Olefins

As indicated above, the present invention, in one embodiment, provides for a combined process for forming methanol and ethanol and converting the methanol and ethanol to light olefins in an OTO reaction system. In such a process an oxygenate feed is contacted with a molecular sieve catalyst under conditions to convert the oxygenate to lower olefins, particularly ethylene and propylene.

Suitable molecular sieves for use in such a process comprise silicates, aluminosilicates and more preferably silicoaluminophosphates. Particularly preferred molecular sieves are those having a crystal framework defined by 8-rings of [TO$_4$] tetrahedra and an average pore size less than about 5 Å, such as in the range of from 3 Å to about 5 Å, for example from 3 Å to about 4.5 Å, and particularly from 3.5 Å to about 4.2 Å. Non-limiting examples of preferred molecular sieves, particularly for converting an oxygenate containing feedstock into olefin(s), include AEL, AFY, AEI, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Although the present application is specifically directed to combining a methanol/ethanol synthesis system with an OTO reaction system, one or more additional components may be included in the feedstock that is directed to the OTO reaction system. For example, the feedstock that is directed to the OTO reaction system optionally contains, in addition to methanol and ethanol, one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehyde, and various acids such as acetic acid.

In addition to the oxygenate component, such as methanol and athanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The OTO process can be conducted over a wide range of temperatures, such as in the range of from about 200° C. to about 100° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the OTO process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kpaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. Pat. No. 6,552,240, which is herein incorporated by reference.

The OTO process is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, New York 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the OTO process is conducted as a fluidized bed process or high velocity fluidized bed process utilizing a reactor system, a regeneration system and a recovery system.

In such a process the reactor system would conveniently include a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the a mount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kpaa) to about 500 psia (3448 kPaa), such as from about 20 psia (138 kpaa) to about 250 psia (1724 kpaa), including from about 25 psia (172 kPaa) to about 150 psia (1034 kpaa), and conveniently from about 30 psia (207 kpaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are disclosed in U.S. Pat. No. 6,290,916 (controlling moisture), which is herein fully incorporated by reference.

The regenerated catalyst composition withdrawn from the regeneration system, preferably from a catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336-337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The invention will now be more particularly described with reference to the Examples, in which all parts are by weight.

In the Examples, hydrotalcites, with MgO contents of 30%, 50%, and 70% respectively, were purchased from Condea. Catalysts were prepared as described below and were then pelletized to a size of 40-80 mesh, diluted with 40-60 mesh quartz particles (1:1 v/v) and tested using the protocols described below.

Catalytic reactions were carried out in a tubular stainless steel reactor (7 mm internal diameter×50 cm in length) fitted with internal thermocouples. The catalyst was loaded in the middle zone of the reactor and was pre-reduced with dilute $H_2$ (2-5% $H_2$ in $N_2$) at a flow rate of 417 cc/min and at a pressure of 150 psi (1034 kPa), following a programmed temperature profile. Unless otherwise noted, all tests were conducted at 750 psi (5171 kPa) and a space velocity of 5000 cc/g cat/hr. A 10-15% (vol) of $N_2$ was used as the internal standard. Both the feed and the reactor effluent were analyzed using a dual-detector (TCD and FID) GC. Total carbon conversion is calculated as:

$$CO_x \text{ conv.} = \{[(CO_{in}+CO_{2in})/N_2 - (CO_{out}+CO_{2out})/N_2]/(CO_{in}+CO_{2in})/N_2\} \times 100\%$$

where "in" represents the feed and "out" represents the product.

Selectivity is reported on the carbon molar base:

$$\text{Sel. } C_m H_n O_p = \{[(wt/MW) \times m]/\text{total moles of carbon in products}\} \times 100\%$$

where wt and MW are the wt % (from FID) and molecular weight respectively of the species being considered. The amount of $CO_2$ formed in the process is excluded from the total moles of carbon in products. When applicable, mass balance was calculated using methanol as a tie point between the TCD and the FID detectors.

EXAMPLE 1 (COMPARATIVE)

Preparation of a Rh/Mn Catalyst Supported on θ-alumina—Catalyst A

An amount of 3 cc of a 10 wt % $Rh(NO_3)_3$ solution in dilute nitric acid (10-25% $HNO_3$ in water) was added drop-wise with stirring to 5 g of θ-alumina to wet the solid. The wet solid was dried at 100° C. for 12 hr and calcined at 350° C. in air for 3 hr and then impregnated with 2 cc of aqueous solution containing 0.49 g of $Mn(NO_3)_2$. The final material was calcined at 350° C. in air for 3 hr. The Rh and Mn loadings were about 3 wt % each.

EXAMPLE 2 (INVENTION)

Preparation of a Rh Catalyst Supported on Hydrotalcite (Mg30)—Catalyst B

An amount of 3 cc of a 10 wt % $Rh(NO_3)_3$ solution in dilute nitric acid (10-25% $HNO_3$ in water) was diluted with 1 cc of water to make a total volume of 4 cc. The solution was added drop-wise with stirring to 5 g of hydrotalcite (Mg30, $[Mg_{0.34}Al_{0.66}(OH)_2](CO_3)_{0.33} \cdot mH_2O$, surface are =271 $m^2/g$) to wet the solid. The wet solid was dried at 110° C. for 20 hr and calcined at 450° C. in air for 8 hr. The Rh loading was about 3 wt %.

EXAMPLE 3 (INVENTION)

Preparation of a Rh Catalyst Supported on Hydrotalcite (Mg50)—Catalyst C

An amount of 3 cc of a 10 wt % $Rh(NO_3)_3$ solution in dilute nitric acid (10-25% $HNO_3$ in water) was added drop-wise with stirring to 5 g of hydrotalcite (Mg50, [Mg$_{0.56}$Al$_{0.44}$(OH)$_2$](CO$_3$)$_{0.22}$.mH$_2$O, surface area=228 m$^2$/g) to wet the solid. The wet solid was dried at 110° C. for 20 hr and calcined at 450° C. in air for 8 hr. The Rh loading was about 3 wt %.

EXAMPLE 4 (INVENTION)

Preparation of a Rh Catalyst Supported on Hydrotalcite (Mg70)—Catalyst D

An amount of 3 cc of a 10 wt % Rh(NO$_3$)$_3$ solution in dilute nitric acid (10-25% HNO$_3$ in water) was added drop-wise with stirring to 5 g of Hydrotalcite (Mg70, [Mg$_{0.78}$Al$_{0.22}$(OH)$_2$](CO$_3$)$_{0.33}$.mH$_2$O, S.A.=201 m$^2$/g) to wet the solid. The wet solid was dried at 110° C. for 20 hr and calcined at 450° C. in air for 8 hr. The Rh loading was about 3 wt %.

EXAMPLE 5 (INVENTION)

Preparation of a Rh Catalyst Supported on Hydrotalcite (Mg30)—Catalyst E

An amount of 0.389 g of Rh(CO)$_2$(acac) was dissolved in 25 cc of acetone to make a solution. The solution was added drop-wise with stirring to 5.185 g of hydrotalcite (Mg30, [Mg$_{0.34}$Al$_{0.66}$(OH)$_2$](CO$_3$)$_{0.33}$.mH$_2$O, surface area=271 m$^2$/g) to wet the solid. Multiple impregnation cycles were necessary in this case and the wet solid was dried at 100° C. for 30 min in between cycles of impregnation. The final material was calcined at 450° C. in air for 8 hr. The Rh loading was about 3 wt %.

EXAMPLE 6 (INVENTION)

Preparation of Rh/Mn Catalyst Supported on Hydrotalcite (Mg30)—Catalyst F

The hydrotalcite (Mg30) used in this example was previously impregnated with 3 wt % rhodium, which was made in the same manner as in Example 5 but not calcined (3% Rh/HT (Mg30)). An amount of 0.408 g of Mn(OAc)$_2$.4H$_2$O was dissolved in 2.0 cc of water and added drop-wise with stirring to 3.054 g of the 3% Rh/HT(Mg30). The wet solid was dried at 100° C. for 10 hr and calcined at 450° C. in air for 8 hr. The Rh and Mn loadings were about 3 wt % each.

EXAMPLE 7 (INVENTION)

Preparation of a Co Catalyst Supported on Hydrotalcite (Mg50)—Catalyst G

An amount of 2.97 g of Co(NO$_3$)$_2$.6H$_2$O was dissolved in 4 cc of water and added drop-wise to 6.03 g of hydrotalcite (Mg50, [Mg$_{0.56}$Al$_{0.44}$(OH)$_2$](CO$_3$)$_{0.22}$.mH$_2$O, surface area=228 m$^2$/g) to wet the solid. The wet solid was dried at 100° C. for 3 hr and calcined at 450° C. in air for 8 hr. The Co loading was about 10 wt %.

EXAMPLE 8 (INVENTION)

Preparation of Co/Cu Catalyst Supported on Hydrotalcite (Mg50)—Catalyst H

The hydrotalcite (Mg50) used in this example was previously impregnated with 10 wt % Co, which was made in the same manner as in Example 7 but not calcined (10% Co/HT (Mg50)). An amount of 1.20 g of Cu(NO$_3$)$_2$.2.5H$_2$O was dissolved in 2.0 cc of water and added drop-wise to 4.10 g of the 10% Co/HT(Mg50). The wet solid was dried at 100° C. for 3 hr and calcined at 450° C. in air for 8 hr. The Cu and Co loadings were about 10 wt % each.

EXAMPLE 9

Catalyst Test Results

The above prepared catalysts were tested for the synthesis of alcohols from two different syngas mixtures: (a) H$_2$/CO/N$_2$=60/30/10 and (b) H$_2$/CO/CO$_2$/N$_2$=57/24/5/14. The results are listed in the following tables. The total alcohol selectivity is the sum of C$_1$—C$_6$OH, the hydrocarbon (HC) is largely methane, and the oxygenates are the total of oxygen-containing products excluding alcohols.

TABLE 1

| (H$_2$/CO/N$_2$ = 60/30/10, 750 psi, 5000 cc/g cat/hr) | | | | | | | | |
|---|---|---|---|---|---|---|---|---|
| Catalyst | A | B | C | D | E | F | G | H |
| T (° C.) | 277 | 294 | 273 | 271 | 301 | 259 | 281 | 278 |
| CO$_x$ conv. | 12.5 | 17.5 | 4.9 | 2.4 | 14.4 | 4.7 | 9.8 | 19.6 |
| Sel. | | | | | | | | |
| CH$_4$ | 66.8 | 41.1 | 40.1 | 25.7 | 42.9 | 23 | 44.7 | 68.3 |
| DME | 0.65 | 1.4 | 0 | 0 | 35.4 | 9.5 | 6.5 | 6.4 |
| MeOH | 0.86 | 30.9 | 37.9 | 56.3 | 12.2 | 56.8 | 6.1 | 3.7 |
| EtOH | 3.99 | 10.5 | 14.7 | 8.8 | 1.4 | 5 | 1.3 | 2.7 |
| Σalcohol | 7.22 | 51.6 | 58 | 74.3 | 15.2 | 66.4 | 24.4 | 16.5 |
| Σoxygenate | 25.9 | 7.3 | 1.9 | 0 | 42.4 | 10.6 | 30.9 | 15.2 |

TABLE 2

| (H$_2$/CO/CO$_2$/N$_2$ = 57/24/5/14, 750 psi, 5000 cc/g cat/hr) | | | | | | | | |
|---|---|---|---|---|---|---|---|---|
| Catalyst | A | B | C | D | E | F | G | H |
| T (° C.) | 277 | 295 | 272 | 272 | 301 | 265 | 281 | 278 |
| CO$_x$ conv. | 11.8 | 13.1 | 1.6 | 2.5 | 10.1 | 3.0 | 11.9 | 6.3 |
| Sel. | | | | | | | | |
| CH$_4$ | 69.7 | 47.3 | 47 | 38.8 | 42.9 | 19.9 | 43.7 | 72 |
| DME | 2.1 | 1.4 | 0 | 0 | 18.4 | 6.1 | 4.8 | 6.0 |
| MeOH | 1.0 | 29.1 | 29.3 | 46.5 | 28.9 | 65.4 | 11.7 | 6.2 |
| EtOH | 4.5 | 14.2 | 15.2 | 9 | 4.6 | 4.8 | 1.7 | 3.0 |
| Σalcohol | 7.7 | 45 | 50 | 58.3 | 35.4 | 74 | 28.6 | 15.9 |
| Σoxygenate | 22.6 | 7.7 | 3.1 | 2.9 | 21.7 | 6.1 | 27.8 | 12 |

While the present invention has been described and illustrated by reference to particular embodiments, those of ordinary skill in the art will appreciate that the invention lends itself to variations not necessarily illustrated herein. For this reason, reference should be made solely to the appended claims for purposes of determining the true scope of the present invention.

We claim:
1. An alcohol synthesis catalyst comprising:
   (a) at least one catalytically active metal or metal compound, active in producing alcohols from synthesis gas, and selected from the group consisting of rhodium, manganese, cobalt, copper, and mixtures thereof; and
   (b) a support for the at least one catalytically active metal or metal compound, wherein the support is an anionic clay comprising a hydrotalcite clay with an average spherical diameter of up to about 60 μm and having the formula:

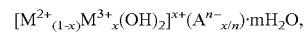

wherein $M^{2+}$ is a metal ion having a valence of 2+, $M^{3+}$ is a metal ion having a valence of 3+, x is a number of about 0.10 to about 0.50, $A^{n-}$ is an anion having a negative charge of n, and m is 0 or a positive number, and wherein $M^{2+}$ and $M^{3+}$ are different from said at least one catalytically active metal or metal compound, with the at least one catalytically active metal or metal compound being on the support.

2. The catalyst of claim 1, wherein said catalytically active metal or metal compound is present in an amount between about 0.01 and about 20 weight % of the total catalyst on an elemental metal basis.

3. The catalyst of claim 1, wherein said catalytically active metal or metal compound is present in an amount between about 1 and about 10 weight % of the total catalyst on an elemental metal basis.

4. The catalyst of claim 1, wherein $M^{2+}$ is a metal ion selected from $Mg^{2+}$, $Ca^{2+}$, $Ni^{2+}$, $Cd^{2+}$, $Co^{2+}$, $Cu^{2+}$, $Fe^{2+}$, $Mn^{2+}$, $Pd^{2+}$, $Pt^{2+}$, $Sr^{2+}$, $Ti^{2+}$, $V^{2+}$, $Zn^{2+}$, $Zr^2$, and mixtures thereof.

5. The catalyst of claim 1, wherein $M^{3+}$ is a metal ion selected from $Al^{3+}$, $B^{3+}$, $Cr^{3+}$, $Fe^{3+}$, $Mn^{3+}$, $Ni^{3+}$, $Co^{3+}$, $Ga^{3+}$, $In^{3+}$, $Rh^{3+}$, $Ti^{3+}$, $Tl^{3+}$, $V^{3+}$, a trivalent lanthanum metal ion, and mixtures thereof.

\* \* \* \* \*